United States Patent [19]

Karsh

[11] 4,063,553

[45] Dec. 20, 1977

[54] PRESSURE TRANSDUCING METHODS AND APPARATUS

[75] Inventor: Herbert Karsh, Laguna Beach, Calif.

[73] Assignee: Bell & Howell Company, Chicago, Ill.

[21] Appl. No.: 674,719

[22] Filed: Apr. 8, 1976

[51] Int. Cl.$^2$ .......................... A61M 5/00; A61B 5/02
[52] U.S. Cl. ............................ 128/214 F; 128/214 E; 128/2.05 D; 55/205
[58] Field of Search ..................... 128/2.05 D, 2.05 E, 128/2.05 R, 214 E, 214 F, 214 R, DIG. 12, DIG. 13; 141/18, 29, 110, 322; 55/204, 205

[56] References Cited

U.S. PATENT DOCUMENTS

| 3,731,680 | 5/1973 | Wright et al. | 128/214 F X |
| 3,807,142 | 4/1974 | Rich et al. | 55/204 X |
| 3,996,027 | 12/1976 | Schnell et al. | 55/205 X |

*Primary Examiner*—Stephen C. Pellegrino

*Attorney, Agent, or Firm*—Benoit Law Corporation

[57] ABSTRACT

Methods and apparatus are disclosed for handling a compatible solution relative to a circulatory system of a living organism with the aid of a catheter and a recipient device having a circular cavity connected to the catheter. The compatible solution is injected into the circular cavity and is rotated in that cavity in a whirl sweeping all regions of the circular cavity and having a peripheral portion encompassing a central axis of the circular cavity and proceeding circumferentially along a peripheral boundary of the circular cavity.

There are also disclosed methods and apparatus for transferring a pressure signal relative to a liquid in a circular cavity. Liquid is injected into the circular cavity and is rotated therein in a whirl sweeping all regions of the circular cavity and having a peripheral portion encompassing a central axis of the circular cavity and proceeding circumferentially along a peripheral boundary of the circular cavity.

18 Claims, 2 Drawing Figures

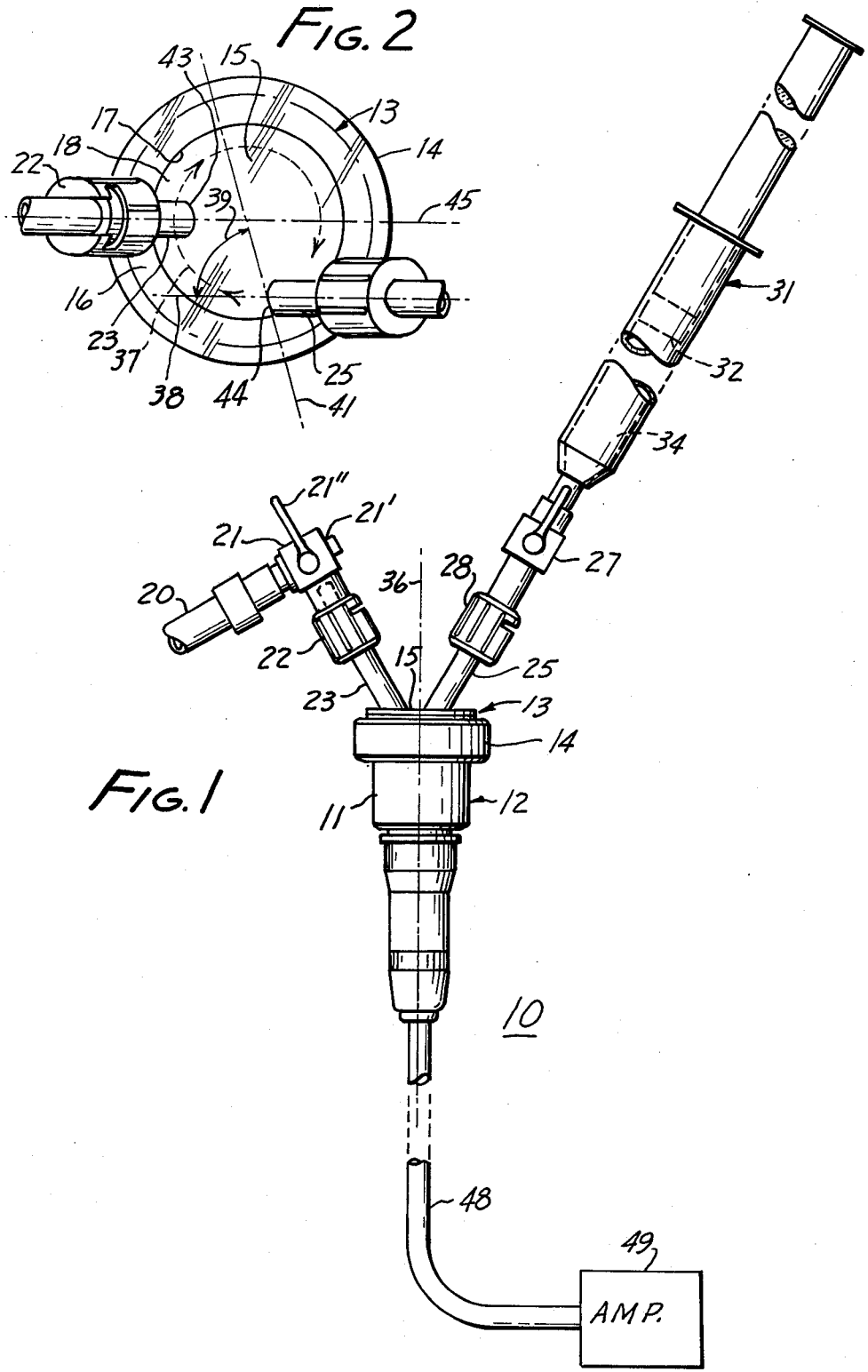

PRESSURE TRANSDUCING METHODS AND APPARATUS

BACKGROUND OF THE INVENTION

1. Field of the Invention

The subject invention relates to pressure transducers and to methods and apparatus for handling a compatible solution relative to the circulatory system of a living organism with the aid of a catheter.

2. Description of the Prior Art

The design and operation of equipment for handling a compatible solution relative to the circulatory system of a living organism shares with the design and operation of liquid pressure transducing devices a concern over the removal of air bubbles from the compatible solution or other liquid. In particular, air bubbles are desired to be kept out of the circulatory system of living organisms. In the case of pressure signal transducing or transferring equipment, the compressible nature of air bubbles diminishes and otherwise degrades the signal. Yet, air bubbles inside liquid-receiving cavities, because of surface tension and other effects, tend to resist externally induced attempts at their removal.

SUMMARY OF THE INVENTION

It is a general object of this invention to overcome the above mentioned disadvantages.

It is a related object of this invention to provide improved methods and apparatus for handling compatible solutions relative to circulatory systems of living organisms.

It is also an object of this invention to provide improved methods and apparatus for transducing a pressure signal relative to a liquid.

It is also an object of this invention to facilitate the removal of air or other gas bubbles in solution or liquid handling equipment.

From one aspect thereof, the subject invention resides in a method of handling a compatible solution relative to a circulatory system of a living organism, with the aid of a catheter insertible into the circulatory system and a recipient device having a circular cavity connected to the catheter at a first predetermined location. The invention according to this aspect resides, more specifically, in the improvement comprising in combination the steps of injecting the compatible solution into the cavity at a second predetermined location situated at a distance from and to one side of a diametrical plane through the circular cavity and the first location, and rotating the injected compatible solution in the circular cavity in a whirl sweeping all regions of the circular cavity and having a peripheral portion encompassing a central axis of the circular cavity and proceeding circumferentially along a peripheral boundary of the circular cavity.

From another aspect thereof, the subject invention resides in a method of transferring a pressure signal relative to a liquid in a circular cavity and, more specifically, resides in the improvement comprising in combination the steps of injecting a liquid into the circular cavity, wiping gas bubbles from boundary surfaces of the circular cavity by rotating the injected liquid in the circular cavity in a whirl sweeping all regions of the circular cavity and having a peripheral portion encompassing a central axis of the circular cavity and proceeding circumferentially along a peripheral boundary of the circular cavity, bleeding gas from the wiped gas bubbles from the circular cavity, and transferring a pressure signal relative to the injected liquid after the gas bubbles have been wiped from the boundary surfaces and the gas has been bled.

From another aspect thereof, the subject invention resides in a method of keeping gas bubbles out of a circulatory system of a living organism connected via a catheter insertible into the circulatory system to a recipient device having a circular cavity connected to the catheter and tending to retain gas bubbles. The invention according to this aspect resides, more specifically, in the improvement comprising in combination the steps of providing a solution compatible with the circulatory system, injecting the compatible solution into the circular cavity, wiping gas bubbles from boundary surfaces of the circular cavity by rotating the injected compatible solution in the circular cavity in a whirl sweeping all regions of the circular cavity and having a peripheral portion encompassing a central axis of the circular cavity and proceeding circumferentially along a peripheral boundary of the circular cavity, and bleeding gas from the wiped gas bubbles from the circular cavity.

From another aspect thereof, the subject invention resides in a method of transferring a pressure signal relative to a liquid in a circular cavity having a first inlet at a first predetermined location. The invention according to this aspect resides, more specifically, in the improvement comprising in combination the steps of injection a liquid into the cavity through a second inlet at a second predetermined location situated at a distance from and to one side of a diametrical plane through the circular cavity and the first location, wiping gas bubbles from boundary surfaces of the circular cavity by rotating the injected liquid in the circular cavity in a whirl sweeping all regions of the circular cavity and having a peripheral portion encompassing a central axis of the circular cavity and proceeding circumferentially along a peripheral boundary of the circular cavity, bleeding gas from the wiped gas bubbles from the circular cavity, and transferring a pressure signal through the first inlet and injected liquid after the gas bubbles have been wiped from the boundary surface and the gas has been bled.

From another aspect thereof, the subject invention resides in apparatus for providing pressure-responsive electric transducer signals relative to a circulatory system of a living organism with the aid of a catheter insertible into the circulatory system and a solution compatible with the circulatory system. The invention according to this aspect resides, more specifically, in the improvement comprising, in combination, means for receiving the solution having a circular cavity enclosed by a circular wall portion, means connected to the receiving means for coupling the catheter to the circular cavity, and means connected to the receiving means for injecting the compatible solution into the circular cavity, the injecting means including means for wiping gas bubbles from boundary surfaces of the circular cavity by rotating the injected compatible solution in the circular cavity in a whirl sweeping all regions of the circular cavity and having a peripheral portion encompassing a central axis of the circular cavity and proceeding along the circular wall portion a blood pressure transducer, means connected to the receiving means for mounting the blood pressure transducer at the circular cavity in pressure signal transferring relationship with the solution, means for bleeding gas from the wiped gas bubbles from the circular cavity and for blocking off the catheter from the circular cavity while the gas is being bled, means for transferring a pressure signal from the circulatory system through the catheter and injected compatible solution to the blood pressure transducer after the gas has been bled, and means for transducing the transferred pressure signal into electric transducer signals.

From yet another aspect thereof, the subject invention resides in apparatus for transducing a pressure signal relative to a liquid and, more specifically, resides in the improvements comprising, in combination, liquid-receiving means defining a circular cavity enclosed by a circular wall portion, means connected to the liquid-receiving means for transferring a liquid to the circular cavity, means connected to the liquid-receiving means for injecting a liquid into the circular cavity and for wiping gas bubbles from boundary surfaces of the circular cavity by rotating the injected liquid in the circular cavity in a whirl sweeping all regions of the circular cavity and having a peripheral portion encompassing a central axis of the circular cavity and proceeding along the circular wall portion a pressure transducer, means connected to the liquid-receiving means for mounting the pressure transducer at the circular cavity, means for bleeding gas from the wiped gas bubbles from the circular cavity and for blocking off the transferring means from the circular cavity while the gas is being bled, and means for transferring a pressure signal through the transferring means and injected liquid to the pressure transducer after the gas has been bled.

From another aspect thereof, the subject invention resides in apparatus for handling a compatible solution relative to a circulatory system of a living organism with the aid of a catheter insertible into the circulatory system. The invention according to this aspect resides, more specifically, in the improvement comprising, in combination, means for receiving the solution having a circular cavity enclosed by a circular wall portion, means connected to the receiving means for coupling the catheter to the circular cavity at a first predetermined location, means connected to the receiving means for injecting the compatible solution into the cavity at a second predetermined location situated at a distance from and to one side of a diametrical plane through the circular cavity and the first location for rotating the injected compatible solution in the circular cavity in a whirl sweeping all regions of the circular cavity and having a peripheral portion encompassing a central axis of the circular cavity and proceeding along the circular wall portion.

From another aspect thereof, the subject invention resides in apparatus for transducing a pressure signal relative to a liquid. The invention according to this aspect resides, more specifically, in the improvement comprising, in combination, liquid-receiving means defining a circular cavity enclosed by a circular wall portion and including a first inlet at a first predetermined location, means connected to the liquid-receiving means for injecting a liquid into the cavity at a second predetermined location situated at a distance from and to one side of a diametrical plane through the circular cavity and the first location for wiping gas bubbles from boundary surfaces of the circular cavity by rotating the injected liquid in the circular cavity in a whirl sweeping all regions of the circular cavity and having a peripheral portion encompassing a central axis of the circular cavity and proceeding along the circular wall portion, means for bleeding gas from the wiped gas bubbles from the circular cavity, and means for transferring a pressure signal through the first inlet and injected liquid.

BRIEF DESCRIPTION OF THE DRAWINGS

The subject invention and its objects will become more readily apparent from the following detailed description of preferred embodiments thereof, illustrated by way of example in the accompanying drawings, in which like reference numerals designate like or functionally equivalent parts, and in which:

FIG. 1 is a side view of part of a blood pressure transducing system embodying the subject invention; and FIG. 2 is a top view, on an enlarged scale, of part of the equipment shown in FIG. 1.

DESCRIPTION OF PREFERRED EMBODIMENTS

The blood pressure transducing system 10 shown in the drawings, has a blood pressure transducer 12 provided with a transparent dome 13 of glass or a suitable plastic. The dome 13 is threaded into a circular nut 14 on the transducer body 11. In the illustrated preferred embodiment, the part 13 has a flat top 15 for minimizing the solution or liquid volume at the transducer. However, the part 13 is still generally referred to as a "dome" and may in fact be dome-shaped.

A circular weight 16 inside the dome 13 defines a circular wall portion 17 of a cavity 18 inside the dome 13 between the top 15 thereof and the diaphragm of the pressure transducer located below the dome 13.

In practice, pressure signals are transferred to the cavity 18 from a living organism via a compatible solution in a catheter 20 which is connected to a shutoff valve 21. A Linden fitting 22 connects the valve 21 to a tube 23 attached to the dome 13 and issuing into the cavity 18 through the top 15. The tube 23 may be attached to the top 15 at the center thereof, or then at a location spaced from the center, such as shown in the drawings.

The transducer 12 includes a second tube 25 which is attached to the dome 13 and issues into the cavity 18. A second shutoff valve 27 is attached to the tube 25 by a Linden fitting 28.

A syringe 31 is attached to the valve 27 and communicates with the cavity 18 through the second tube 25 when the valve 27 is opened. The syringe 31 has a piston 32 for applying to the cavity 18 a solution that is physiologically compatible with the blood in the living organism to which the catheter is connected in practice.

Depending on the condition of the living organism and the purpose to be accomplished, the compatible solution 34 in the syringe 31 may, for instance, be a saline or a dextrose solution.

In the operation of the equipment, the compatible solution 34 is injected with the syringe 31 through the second tube 25 into the circular cavity 18 and is rotated in that circular cavity in a whirl sweeping all regions of the circular cavity and having a peripheral portion encompassing a central axis 36 of the circular cavity 18 and proceeding circumferentially along a peripheral boundary or circular wall portion 17. In particular, the compatible solution 34 is preferably injected into the circular cavity 18 in a trajectory 37 having a tangential plane 38 extending at an angle 39 to a diametrical plane 41 through the circular cavity 18 and the beginning of the trajectory 37. As shown in FIG. 2, the tangential plane 38 of the circular trajectory 37 extends preferably at an acute angle to the peripheral boundary or circular wall portion 17 of the cavity 18.

Further in accordance with the illustrated preferred embodiment, the catheter 20 is connected by the first tube 23 to the cavity 18 at a first predetermined location 43. The compatible solution 34 is injected into the cavity 18 through the second tube 25 at a second predetermined location 44 situated at a distance from and to one side of a diametrical plane 45 through the circular cavity 18 and the first location 43.

The resulting whirl sweeps all parts of the dome and wipes air and other gas bubbles from the circular wall portion 17 and from other boundary surfaces including the dome 13 of the cavity before the moving solution reaches the tube 23. In practice, the removed gas bubbles may be bled to atmosphere through the tube 23 and an outlet 21' in the valve 21. To this end, the valve 21 is a three-way valve being manually actuable via a handle 21" between a first position in which the tube 23 is vented to atmosphere via outlet 21' with the catheter 20 being then blocked off from the cavity 18, and an alternative second position in which the outlet 21' is blocked off and the catheter 20 connected to the cavity 18.

The result of the above mentioned sweeping operation is an air and gas free solution or liquid-filled cavity 18 at which the transducer is mounted by means of the circular nut 14.

In practice, the injection of the compatible solution 32 through the tube 25 and cavity 18 is continued through the tube 23 and catheter 20 after the air bubbles have been removed as described above and the catheter has been connected to the tube by actuation of the handle 21". Preferably, this injection continues until the injected solution has reached the tip of the catheter 20 to interface with the blood in the circulatory system for a transfer of pressure signals to the transducer 11.

The pressure-responsive electric transducer signals are conducted by a cable 48 to a signal amplifier and other electrical or electronic measuring equipment 49.

If desired, the angle between the central axis 36 and the first tube may be made larger or smaller than as shown in the drawings. Similarly, the angle between the flat top 15 and the second tube 25 may be made different from what is shown in FIG. 1, as long as that angle remains such that all regions of the cavity 18, including all portions of the dome are swept by the injected solution for the removal of air bubbles.

It should be recognized that the utility of the methods and apparatus herein disclosed is not limited to the blood pressure transducer field, but extends to other solution or liquid handling equipment. Moreover, the utility of the invention extends also to arts in which a pressure signal is transduced relative to a liquid.

In these cases the removal and resultant lack of air or gas bubbles improves the transfer of a pressure signal from the liquid to a transducer, as well as the transfer of a pressure signal into the liquid from a pressure signal generating device.

Depending on the nature of the liquid applied through the inlet 23, the solution or liquid 34 may be of the same type or identical to that applied liquid.

The subject disclosure will suggest or render apparent various modifications or variations within the spirit and scope of the invention to those skilled in the art.

I claim:

1. In a method of keeping gas bubbles out of a circulatory system of a living organism connected via a catheter insertible into said circulatory system to a recipient device having a circular cavity connected to said catheter and tending to retain gas bubbles, the improvement comprising in combination the steps of:

providing a solution compatible with said circulatory system;

injecting said compatible solution into said circular cavity;

wiping gas bubbles from boundary surfaces of said circular cavity by rotating said injected compatible solution in said circular cavity in a whirl sweeping all regions of said circular cavity and having a peripheral portion encompassing a central axis of said circular cavity and proceeding circumferentially along a peripheral boundary of said circular cavity; and bleeding gas from said wiped gas bubbles from said circular cavity.

2. A method as claimed in claim 1, wherein:

said compatible solution is injected into said circular cavity in a trajectory having a tangential plane extending at an angle to a diametrical plane through said circular cavity and the beginning of said trajectory.

3. A method as claimed in claim 1, wherein:

said compatible solution is injected into said circular cavity in a trajectory having a tangential plane extending at an acute angle to said peripheral boundary of said circular cavity.

4. In a method of handling a compatible solution relative to a circulatory system of a living organism, with the aid of a catheter insertible into said circulatory system and a recipient device having a circular cavity connected to said catheter at a first predetermined location, the improvement comprising in combination the steps of:

injecting said compatible solution into said cavity at a second predetermined location situated at a distance from and to one side of a diametrical plane through said circular cavity and said first location; and rotating said injected compatible solution in said circular cavity in a whirl sweeping all regions of said circular cavity and having a peripheral portion encompassing a central axis of said circular cavity and proceeding circumferentially along a peripheral boundary of said circular cavity.

5. A method as claimed in claim 1, including the step of:

effecting a blood pressure measurement at said circular cavity after said gas bubbles have been wiped from said boundary surfaces and said gas has been bled.

6. In a method of transferring a pressure signal relative to a liquid in a circular cavity, the improvement comprising in combination the steps of:

injecting a liquid into said circular cavity;

wiping gas bubbles from boundary surfaces of said circular cavity by rotating said injected liquid in said circular cavity in a whirl sweeping all regions of said circular cavity and having a peripheral portion encompassing a central axis of said circular cavity and proceeding circumferentially along a peripheral boundary of said circular cavity;

bleeding gas from said wiped gas bubbles from said circular cavity; and transferring a pressure signal relative to said injected liquid after said gas bubbles have been wiped from said boundary surfaces and said gas has been bled.

7. A method as claimed in claim 6, wherein:
said liquid is injected into said circular cavity in a trajectory having a tangential plane extending at an angle to a diametrical plane through said circular cavity and the beginning of said trajectory.

8. A method as claimed in claim 6, wherein:
said liquid is injected into said circular cavity in a trajectory having a tangential plane extending at an acute angle to said peripheral boundary of said circular cavity.

9. In a method of transferring a pressure signal relative to a liquid in a circular cavity having a first inlet at a first predetermined location, the improvement comprising in combination the steps of:
injecting a liquid into said cavity through a second inlet at a second predetermined location situated at a distance from and to one side of a diametrical plane through said circular cavity and said first location;
wiping gas bubbles from boundary surfaces of said circular cavity by rotating said injected liquid in said circular cavity in a whirl sweeping all regions of said circular cavity and having a peripheral portion encompassing a central axis of said circular cavity and proceeding circumferentially along a peripheral boundary of said circular cavity;
bleeding gas from said wiped gas bubbles from said circular cavity; and
transferring a pressure signal through said first inlet and injected liquid after said gas bubbles have been wiped from said boundary surface and said gas has been bled.

10. A method as claimed in claim 6, including the step of:
effecting a liquid pressure measurement at said circular cavity after said gas bubbles have been wiped from said boundary surfaces and said gas has been bled.

11. In apparatus for providing pressure-responsive electric transducer signals relative to a circulatory system of a living organism with the aid of a catheter insertible into said circulatory system and a solution compatible with said circulatory system, the improvement comprising in combination:
means for receiving said solution having a circular cavity enclosed by a circular wall portion;
means connected to said receiving means for coupling said catheter to said circular cavity;
means connected to said receiving means for injecting said compatible solution into said circular cavity, said injecting means including means for wiping gas bubbles from boundary surfaces of said circular cavity by rotating said injected compatible solution in said circular cavity in a whirl sweeping all regions of said circular cavity and having a peripheral portion encompassing a central axis of said circular cavity and proceeding along said circular wall portion;
a blood pressure transducer;
means connected to said receiving means for mounting said blood pressure transducer at said circular cavity in pressure signal transferring relationship with said solution;
means for bleeding gas from said wiped gas bubbles from said circular cavity and for blocking off said catheter from the circular cavity while said gas is being bled;
means for transferring a pressure signal from said circulatory system through said catheter and injected compatible solution to said blood pressure transducer after said gas has been bled; and
means for transducing said transferred pressure signal into electric transducer signals.

12. An apparatus as claimed in claim 11, wherein:
said injecting means include means for injecting said compatible solution into said circular cavity at a predetermined location and in a direction extending at an angle to a diametrical plane through said circular cavity and said predetermined location.

13. An apparatus as claimed in claim 11, wherein:
said injecting means include means for injecting said compatible solution into said circular cavity at a predetermined location and in a direction extending at an acute angle to said circular wall portion.

14. In apparatus for handling a compatible solution relative to a circulatory system of a living organism with the aid of a catheter insertible into said circulatory system, the improvement comprising in combination:
means for receiving said solution having a circular cavity enclosed by a circular wall portion;
means connected to said receiving means for coupling said catheter to said circular cavity at a first predetermined location;
means connected to said receiving means for injecting said compatible solution into said cavity at a second predetermined location situated at a distance from and to one side of a diametrical plane through said circular cavity and said first location for rotating said injected compatible solution in said circular cavity in a whirl sweeping all regions of said circular cavity and having a peripheral portion encompassing a central axis of said circular cavity and proceeding along said circular wall portion.

15. In apparatus for transducing a pressure signal relative to a liquid, the improvement comprising in combination:
liquid-receiving means defining a circular cavity enclosed by a circular wall portion;
means connected to said liquid-receiving means for transferring a liquid to said circular cavity;
means connected to said liquid-receiving means for injecting a liquid into said circular cavity and for wiping gas bubbles from boundary surfaces of said circular cavity by rotating said injected liquid in said circular cavity in a whirl sweeping all regions of said circular cavity and having a peripheral portion encompassing a central axis of said circular cavity and proceeding along said circular wall portion;
a pressure transducer;
means connected to said liquid-receiving means for mounting said pressure transducer at said circular cavity;
means for bleeding gas from said wiped gas bubbles from said circular cavity and for blocking off said transferring means from the circular cavity while said gas is being bled; and
means for transferring a pressure signal through said transferring means and injected liquid to said pressure transducer after said gas has been bled.

16. An apparatus as claimed in claim 15, wherein:
said injecting means include means for injecting a liquid into said circular cavity at a predetermined location and in a direction extending at an angle to a diametrical plane through said circular cavity and said predetermined location.

17. An apparatus as claimed in claim 15, wherein:
said injecting means include means for injecting a liquid into said circular cavity at a predetermined location and in a direction extending at an acute angle to said circular wall portion.

18. In apparatus for transducing a pressure signal relative to a liquid, the improvement comprising in combination:
liquid-receiving means defining a circular cavity enclosed by a circular wall portion and including a first inlet at a first predetermined location;
means connected to said liquid-receiving means for injecting a liquid into said cavity at a second predetermined location situated at a distance from and to one side of a diametrical plane through said circular cavity and said first location for wiping gas bubbles from boundary surfaces of said circular cavity by rotating said injected liquid in said circular cavity in a whirl sweeping all regions of said circular cavity and having a peripheral portion encompassing a central axis of said circular cavity and proceeding along said circular wall portion;
means for bleeding gas from said wiped gas bubbles from said circular cavity; and
means for transferring a pressure signal through said first inlet and injected liquid.

* * * * *